(12) United States Patent
Borrello

(10) Patent No.: US 11,904,094 B2
(45) Date of Patent: Feb. 20, 2024

(54) PRESSURE AND OXYGEN MIX CONTROL FOR SINGLE LIMB NON-INVASIVE VENTILATION

(71) Applicant: KONINKLIJKE PHILIPS N.V., Eindhoven (NL)

(72) Inventor: Michael Anthony Borrello, Carlsbad, CA (US)

(73) Assignee: Koninklijke Philips N.V., Eindhoven (NL)

(*) Notice: Subject to any disclaimer, the term of this patent is extended or adjusted under 35 U.S.C. 154(b) by 804 days.

(21) Appl. No.: 16/930,486

(22) Filed: Jul. 16, 2020

(65) Prior Publication Data

US 2021/0069437 A1 Mar. 11, 2021

Related U.S. Application Data

(60) Provisional application No. 62/897,641, filed on Sep. 9, 2019.

(51) Int. Cl.
*A61M 16/00* (2006.01)
*A61M 16/20* (2006.01)

(52) U.S. Cl.
CPC ...... *A61M 16/024* (2017.08); *A61M 16/0066* (2013.01); *A61M 16/204* (2014.02);
(Continued)

(58) Field of Classification Search
CPC ............ A61M 16/0066; A61M 16/204; A61M 2202/0208; A61M 2205/3331;
(Continued)

(56) References Cited

U.S. PATENT DOCUMENTS 5,632,269 A * 5/1997 Zdrojkowski ..... A61M 16/0069
128/204.23
5,740,795 A * 4/1998 Brydon ............... A61M 16/024
128/204.23

(Continued)

FOREIGN PATENT DOCUMENTS

FR 2987274 A1 * 8/2013 ............ A61M 16/00
WO WO-2017055995 A1 * 4/2017 ........ A61M 16/0069

OTHER PUBLICATIONS

Machine Translation of FR 2987274 A1 Accessed Apr. 4, 2023 (Year: 2023).*

(Continued)

*Primary Examiner* — Elliot S Ruddie
(74) *Attorney, Agent, or Firm* — Daniel H. Brean

(57) ABSTRACT

A method for controlling oxygen mix for a single-limb non-invasive ventilator comprising a pressure controller, and both a blower and a pressurized oxygen source downstream of the blower, each comprising a controller and a flow valve controlling flow, comprising: (i) generating a flow trajectory; (ii) providing the generated flow trajectory to a pair of complimentary flow coupling filters comprising a blower flow coupling filter and an oxygen flow coupling filter; (iii) generating an output from each of the filters, comprising an input flow trajectory for the blower flow controller and an input flow trajectory for the oxygen flow controller; and (iv) adjusting, by the blower flow controller and/or oxygen flow controller based on the input flow trajectory, target pressure, and oxygen mix, the blower speed controller and/or the pressurized oxygen source proportional flow valve.

15 Claims, 14 Drawing Sheets

(52) U.S. Cl.
CPC .............. *A61M 2202/0208* (2013.01); *A61M 2205/3331* (2013.01); *A61M 2205/75* (2013.01)

(58) Field of Classification Search
CPC ...... A61M 2205/75; A61M 2016/0027; A61M 2016/0039; A61M 16/0883; A61M 16/125; A61M 16/203; A61M 2205/3334; A61M 2205/3365; A61M 16/10; A61M 16/12; A61M 16/1005; A61M 16/1012; A61M 16/1022; A61M 2016/1025; A61M 16/021–026; A61M 16/122; A61M 16/10125; A61M 16/0057–0072; A61M 2016/0033; A61M 2205/50; A61M 16/0677; A61M 16/0069; A61M 2205/3569; A61M 2205/3592; H03H 11/1204; H03H 11/1269
See application file for complete search history.

(56) References Cited

U.S. PATENT DOCUMENTS

| | | | |
|---|---|---|---|
| 2003/0079750 A1* | 5/2003 | Berthon-Jones | A61M 16/00 128/204.18 |
| 2006/0225737 A1* | 10/2006 | Iobbi | A61M 16/026 128/204.22 |
| 2009/0165795 A1* | 7/2009 | Nadjafizadeh | A61M 16/0666 128/204.26 |
| 2013/0239968 A1 | 9/2013 | Daescher et al. | |
| 2016/0287824 A1 | 10/2016 | Chang | |
| 2018/0280654 A1 | 10/2018 | Borrello | |

OTHER PUBLICATIONS

Borrello, M. et al., "Oxygen ratio control in critical care ventilation using compressed oxygen and blower gas sources", 2020 American Control Conference, (Jul. 1, 2020), Abstract.
International Search Report for PCT/EP2020/074175 dated Aug. 31, 2020.

* cited by examiner

PRESSURE AND OXYGEN MIX CONTROL FOR SINGLE LIMB NON-INVASIVE VENTILATION

CROSS-REFERENCE TO RELATED APPLICATIONS

This patent application claims the priority benefit under 35 U.S.C. § 119(e) of U.S. Provisional Application No. 62/897,641, filed on Sep. 9, 2019, the contents of which are herein incorporated by reference.

BACKGROUND OF THE INVENTION

1. Field of the Invention

The present disclosure is directed generally to methods and systems for controlling pressure and oxygen mix for single limb non-invasive ventilators using a blower as an air source and compressed oxygen gas effused downstream of the blower outlet.

2. Description of the Related Art

Currently, the practice of ventilator design engineering most often employs compressed gas valves as the prime movers; the devices that actuate flow. Compressed air and oxygen from hospital plumbing, typically ranging 50 to 100 psig, supply the valve gas inlets. The valves throttle flow by electronic feedback controls into a manifold. This conveys the mixed gas into the patient circuit that connects the ventilator to the patient airway. Simple algebraic proportioning of total flow between the valves achieves the desired mix at the same time that volume or pressure targets are met with minimal complications. Both the oxygen and air valves are the same and so statically and dynamically matched. By matching, the valves do not compete with one another in pushing gas into the manifold and thus achieve desired mix, pressure and volume.

More recent ventilator designs may use blowers, fans or reciprocating pistons as a prime mover. As long as the inlet gas to these devices is pre-mixed (using a mechanical blender for example or oxygen injected from a compressed gas valve), then the task of controlling mix and pressure is still somewhat independent from one another. The blower, for example serves as the sole actuator to achieve pressure or volume if oxygen is combined with air on the upstream (inlet) side of the blower. In this case the oxygen source has no effect on building pressure in the manifold.

But if oxygen is introduced on the downstream side of the blower (outlet) then both the blower and the oxygen valve become shared prime movers; they both directly affect pressure in the manifold where gases are mixed. The problem with shared action is that the typical blower and compressed gas valve are grossly mismatched dynamically. The blower flow cannot respond nearly as quickly as the valve, and the blower source impedance is much higher than the valve. High source impedance means the blower cannot push gas into the load as easily as the valve is able to do. During the transient, the valve can overcome the blower causing its flow to momentarily reverse. The mix and pressure physical transfer functions become entangled, interfering with one another. This makes the control much more difficult, particularly at high mix settings.

Accordingly, there is a need in the art for single limb non-invasive ventilation systems that use a blower as an air source and compressed oxygen gas effused downstream of the blower outlet, but allow for fast, efficient, and cost-effective mechanisms for controlling pressure and oxygen mix.

SUMMARY OF THE INVENTION

The present disclosure is directed to inventive methods and systems for controlling pressure and oxygen mix for single limb non-invasive ventilators using a blower as an air source and compressed oxygen gas effused downstream of the blower outlet. Various embodiments and implementations herein are directed to a non-invasive ventilator system comprising a pressure controller, both a blower and a pressurized oxygen source where the pressurized oxygen source is downstream of the blower, with each of the blower and the pressured oxygen source comprising a controller and a proportional flow valve controlling flow. A total flow trajectory is generated from an output of the blower pressure controller, and is provided to a pair of complimentary flow coupling filters comprising a blower flow coupling filter and an oxygen flow coupling filter. The filters generate an input flow trajectory for the blower flow controller and an input flow trajectory for the pressurized oxygen source flow controller, and the blower flow controller and/or pressurized oxygen flow controller adjust the blower speed and/or the pressurized oxygen source proportional flow valve based on the input flow trajectory and a target pressure and target oxygen mix.

Generally in one aspect, a method for controlling oxygen mix for a single-limb non-invasive ventilator is provided. The single-limb non-invasive ventilator comprises a pressure controller, both an air blower and a pressurized oxygen source where the oxygen source is downstream of the air blower, each of the air blower and pressurized oxygen source comprising a controller, and the oxygen source comprising a proportional flow valve controlling flow. The method includes: (i) receiving, by the ventilator, a target pressure and target oxygen mix; (ii) generating, from an output of the blower pressure controller, a total flow trajectory; (iii) providing the generated total flow trajectory from the blower pressure controller to a pair of complimentary flow coupling filters, the pair of complimentary flow coupling filters comprising a blower flow coupling filter and an oxygen flow coupling filter; (iv) generating an output from each of the blower flow coupling filter and the oxygen flow coupling filter, comprising an input flow trajectory for the blower flow controller and an input flow trajectory for the pressurized oxygen source flow controller, respectively; and (v) adjusting, by the blower flow controller and/or oxygen flow controller based on the input flow trajectory and the received target pressure and target oxygen mix, the air blower speed and/or the pressurized oxygen source proportional flow valve.

According to an embodiment, the oxygen flow coupling filter comprises a low-pass coupling filter. According to an embodiment, the blower flow coupling filter comprises a higher-pass coupling filter relative to the oxygen flow coupling filter. According to an embodiment, the pair of complimentary flow coupling filters is configured to be complimentary to partition actuator influence over different bands of frequency and the different bands are determined according to the mix target.

According to an embodiment, the blower pressure controller comprises a multi-level cascade feedback architecture.

According to an embodiment, the single-limb non-invasive ventilator further comprises a complimentary filter in feedback with the pressure controller, the complimentary filter configured to receive a pressure measurement from a ventilator pressure sensor and to receive a proximal pressure measurement from a proximal pressure sensor of the patient circuit. According to an embodiment, the complimentary filter is configured to generate a single pressure signal to the pressure controller by blending the received pressure measurement from the ventilator pressure sensor and the received proximal pressure measurement from the proximal pressure sensor. According to an embodiment, the complimentary filter is configured to blend the received pressure measurements using complimentary frequency bands with the proximal pressure sensor signal at a low frequency and the ventilator pressure sensor signal at a higher frequency.

According to an aspect is provided a single-limb non-invasive ventilator system configured to control oxygen mix pursuant to a target pressure and target oxygen mix. The system includes: (i) a pressure controller configured to generate a total flow trajectory; (ii) an air blower comprising a blower flow controller; (iii) a pressurized oxygen source downstream of the air blower and comprising an oxygen controller and a proportional flow valve controlling oxygen flow; (iv) a pair of complimentary flow coupling filters, the pair of complimentary flow coupling filters comprising a blower flow coupling filter and an oxygen flow coupling filter; and (v) a controller configured to: provide the generated total flow trajectory from the blower pressure controller to the pair of complimentary flow coupling filters; and receive an output from each of the blower flow coupling filter and the oxygen flow coupling filter, comprising an input flow trajectory for the blower flow controller and an input flow trajectory for the pressurized oxygen source flow controller, respectively; where the blower flow controller and/or oxygen flow controller adjust, based on the input flow trajectory and the target pressure and target oxygen mix, the blower speed and/or the pressurized oxygen source proportional flow valve.

According to an embodiment, the single-limb non-invasive ventilator system further includes a complimentary filter in feedback with the pressure controller, the complimentary filter configured to receive a pressure measurement from a ventilator pressure sensor and to receive a proximal pressure measurement from a proximal pressure sensor of a patient circuit. According to an embodiment, the complimentary filter is configured to generate a single pressure signal to the pressure controller by blending the received pressure measurement from the ventilator pressure sensor and the received proximal pressure measurement from the proximal pressure sensor. According to an embodiment, the complimentary filter is configured to blend the received pressure measurements using complimentary frequency bands with the proximal pressure sensor signal at a low frequency and the ventilator pressure sensor signal at a higher frequency.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EXEMPLARY EMBODIMENTS

Figure 1:
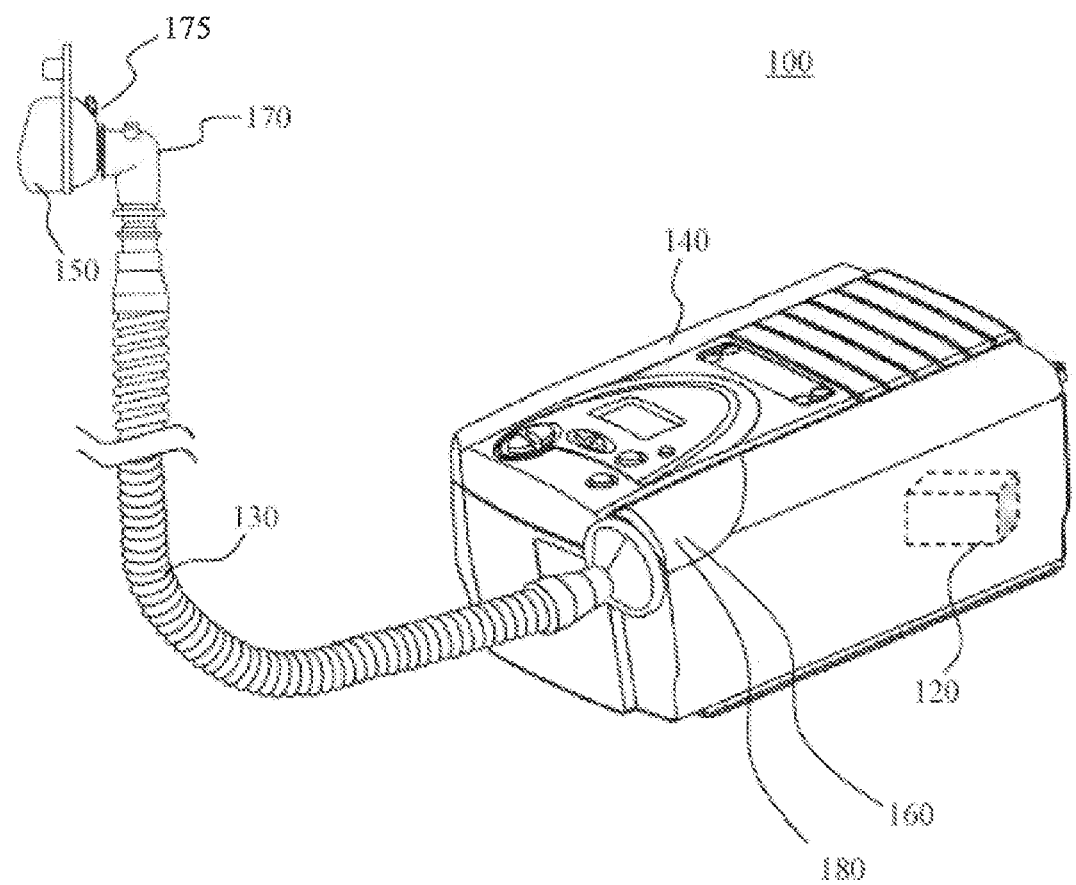
FIG. 1 is a schematic representation of a non-invasive ventilator system in accordance with an embodiment.

The present disclosure describes various embodiments of a non-invasive ventilator ("NIV") system and method. More generally, Applicant has recognized and appreciated that it would be beneficial to provide a non-invasive ventilator system and method that accurately and quickly controls pressure and oxygen mix for single limb non-invasive ventilators using a blower as an air source and compressed oxygen gas effused downstream of the blower outlet. For example, the non-invasive ventilator system comprises a pressure controller, both a blower and a pressurized oxygen source where the pressurized oxygen source is downstream of the blower, with each of the blower and the pressurized oxygen source comprising a controller and a proportional flow valve controlling flow. A total flow trajectory is generated from an output of the blower pressure controller, and is provided to a pair of complimentary flow coupling filters comprising a blower flow coupling filter and an oxygen flow coupling filter. The filters generate an input flow trajectory for the blower flow controller and an input flow trajectory for the pressurized oxygen source flow controller, and the blower flow controller and/or oxygen flow controller adjust the blower speed and/or the pressurized oxygen source proportional flow valve based on the input flow trajectory and a target pressure and target oxygen mix.

The non-invasive ventilator system and method disclosed or otherwise envisioned herein provides numerous advantages over the prior art. Combining blower and valve flow controls considerably increases complexity in the control algorithms mainly in terms of stability, accuracy, and uniformity of control response. Valves can overpower a blower. And while gas flow cannot reverse direction through a compressed gas valve, it is possible in the case of a blower. The dynamic response between blower and valve can be significant as well as the differences in the flow source output impedance (ability to drive flow into the load). The level of control complexity largely depends on an architectural choice of the gas pathways, and specifically the relative location of the blower and oxygen gas valve to one another.

Any architecture that combines blower and valve flow controls has numerous other technical problems. For example, the blower flow response time is typically much slower than the response time of the valve since the blower inertia requires significantly more time to accelerate and establish flow; for a valve the energy is all stored in the compression of the gas. The slower response of the blower itself affects the pressure response time in general, but the flow-dynamic mismatch between blower and valve makes pressure and mix controls a challenging problem. Further, requirements often specify that the target pressure set by the user be accurate at the patient connection. Although a proximal pressure sense line is typically provided in a single-limb non-invasive ventilation (NIV), using that pressure alone as the source for control introduces significant delay in the pressure feedback loop. To compensate for delay, loop gain must be limited. This further slows the blower response.

Additionally, using a blower speed control can improve response, but tachometer signals tend to drop out at low speed. An observer that uses current and voltage can be used to solve drop out, but at higher speeds beyond the sampling rate torque commutation ripple frequencies can be aliased back into the control band causing instability.

As with any control system, the effects of disturbance must be taken into account as part of the design to make sure the controls follow the desired target pressure in spite of the disturbance, and that the controls attenuate rather than amplify disturbance. For NIV disturbances sources include (a) flow disturbance (demand) from the patient (b) perturbations in the patient connection (leaks and partial occlusions) and (c) torque disturbances from the blower motor bearings and aerodynamic pressure load.

Additionally, patient exhaled gas that can flow back through the blower to ambient can 'pre-load' the blower pathway with gas enriched in oxygen. Subsequent rebreathing of the gas introduces additional oxygen over the desired set-point, further making mix control a challenging problem.

Ventilator controls often apply proportional-integral-derivative (PID) compensators to stabilize and shape the transient response. For fixed gain controls, variations in the patient pressure-flow dynamics result in vast differences in transient response and end inspiratory pressure accuracy due to overshoot. The PID architecture itself can be the cause of overshoot since it applies either two real or a complex pair of 'zeros' in the design which persist to act in the closed loop.

Several versions or alternate, customized controller structures are often required in the ventilator to serve specific areas of ventilation. For example, prior ventilator designs have applied separate controllers to serve breath delivery, system services or diagnostics, standby mode, and in some cases different controllers for neonatal, pediatric and adult patients. While this can be an effective method, it doubles, triples or quadruples the complexity making maintenance of design, testing and software changes more difficult to manage.

The methods and systems described or otherwise envisioned herein address and resolve these issues. While some ventilators use separate gains or structures depending on patient size, circuit size, type, specific ventilator settings etc., the invention described herein claims effective control with a single structure. This extends to auxiliary functions as well such as controllers used in calibration, system services and standby states.

Referring to FIG. 1, in one embodiment, is a representation of an example non-invasive ventilation system 100. The system includes a gas source which can be any gas, including but not limited to atmospheric air and oxygen, among others. According to an embodiment, the non-invasive ventilation system 100 comprises a blower as an air source and compressed oxygen gas effused downstream of the blower outlet. The system also includes a controller 120, which is a conventional microprocessor, an application specific integrated circuit (ASIC), a system on chip (SOC), and/or a field-programmable gate arrays (FPGA), among other types of controllers. A controller may be implemented with or without employing a processor, and also may be implemented as a combination of dedicated hardware to perform some functions and a processor (e.g., one or more programmed microprocessors and associated circuitry) to perform other functions.

The controller 120 can be coupled with or otherwise in communication with any needed memory, power supply, I/O devices, control circuitry, sensors, valves, blowers, and/or other devices necessary for operation of the ventilator according to the embodiments described or otherwise envisioned herein. For example, in various implementations, a processor or controller may be associated with one or more storage media. In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

According to an embodiment, the controller 120 is configured or programmed to function as a blower controller to coordinate and control the blower functions of the non-invasive ventilator. For example, the blower controller can control the rate and strength of the blower(s) of the system, thereby controlling or directing the flow through the circuit. According to another embodiment, the blower controller is a separate component, preferably in communication with controller 120, although the multiple functions of the system can be otherwise coordinated. Although this embodiment uses the blower flow controller to excite the circuit, any type of flow source, including for example proportionally controlled compressed gas valves, could be utilized where the source provides a means of actual flow and pressure measurements.

The non-invasive ventilator includes a tube or patient circuit 130 that delivers gas from the remote ventilator component 140 to the patient interface 150. Patient interface 150 can be, for example, a face mask that covers all or a portion of the patient's mouth and/or nose. There may be masks of many different sizes to accommodate patients or individuals of different sizes, and/or the mask may be adjustable. As another alternative, patient interface 150 may fit within or on, or otherwise interact with, a tracheostomy tube. Accordingly, the patient interface 150 may be a variety of sizes to accommodate tracheostomies of different shapes and sizes. The patient interface is configured to fit with at least a portion of the patient's airway and includes an exhalation port 175. The single-limb non-invasive ventilation system comprises a distal gas flow sensor 160 at the end of the tubing near the remote ventilator component 140, a proximal pressure sensor 170 at the end of the tubing near the patient interface 150, and a distal (machine) sensor 180 near the distal gas flow sensor 160. Either of distal gas flow sensor 160 or proximal pressure sensor 170 may comprise, for example, two or more sensors. For example, distal gas flow sensor 160 can comprise a blower flow sensor and an O2 valve sensor. Further, any of the sensors may be external or internal to the ventilator. Controller 120 is configured to receive sensor data from both distal gas flow sensor 160, distal pressure sensor 180, and proximal pressure sensor 170, either through wired or wireless communication. According to an embodiment, the proximal pressure sensor can physically be attached at the patient connection and communicate back to the processor electrically, or it can be located in the ventilator where a length of small diameter tubing is connected from this sensor back to the patient connection. The embodiments described herein, for example, address the delay that tubing introduces.

Figure 2:
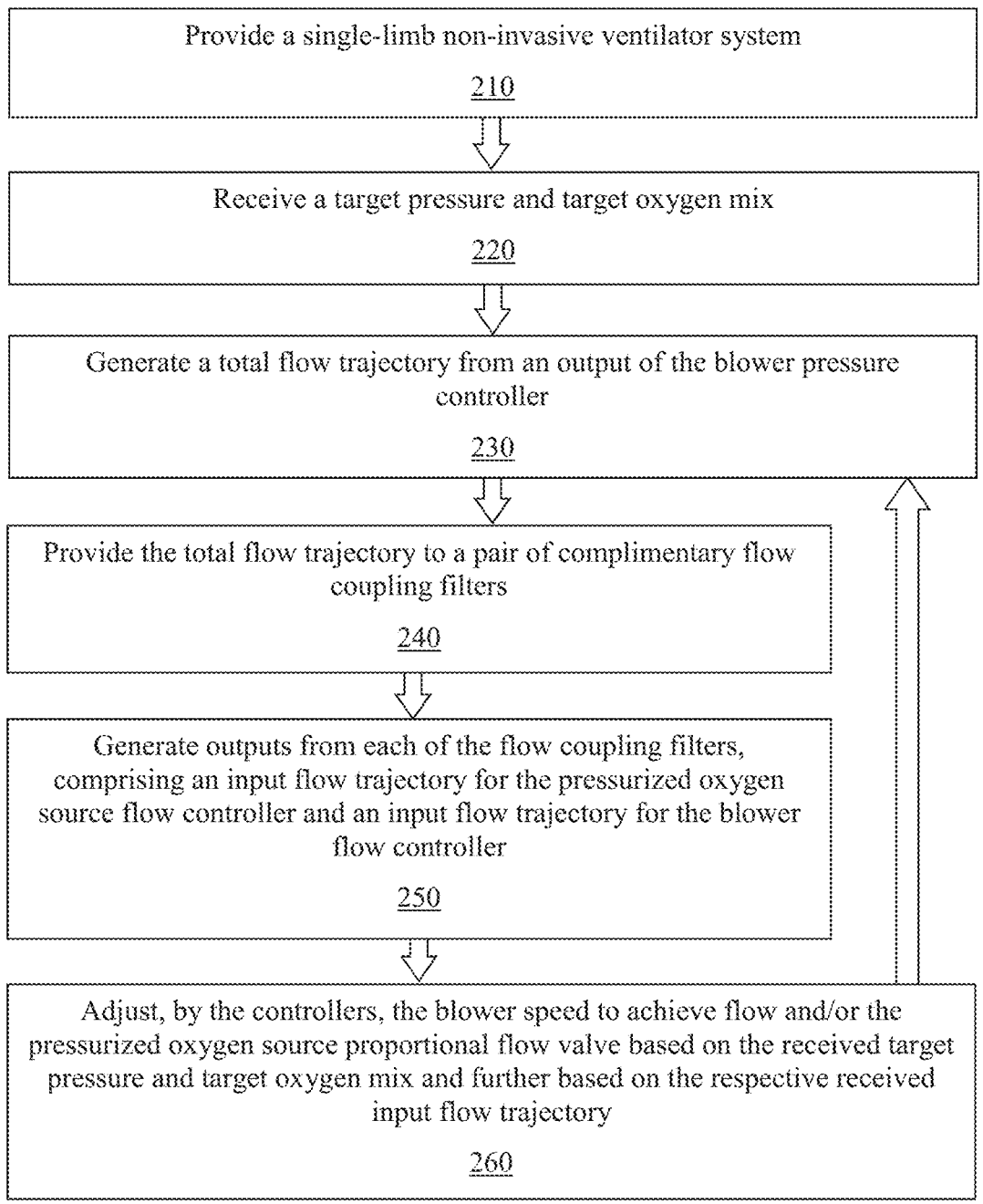
FIG. 2 is a flowchart of a method for controlling pressure and oxygen mix for a single limb non-invasive ventilator, in accordance with an embodiment.

Referring to FIG. 2, in one embodiment, is a flowchart of a method 200 for controlling pressure and oxygen mix for single limb non-invasive ventilators. At step 210, a non-invasive ventilator system 100 is provided. The non-invasive ventilator system can be any of the embodiments described or otherwise envisioned herein. At step 220, the system receives a target pressure and target oxygen mix. The target pressure and target oxygen mix can be any desired pressure and mix and will depend upon the needs of the patient and the healthcare professional. The target pressure and target oxygen mix can be received using any input method, including via a user interface or any other method.

At step 230 of the method, the system generates a total flow trajectory from an output of the blower pressure controller of the system. A total flow trajectory can be calculated using any of the methods disclosed or otherwise envisioned herein.

At step 240 of the method, the total flow trajectory generated from the blower pressure controller of the system is provided to a pair of complimentary flow coupling filters, the pair of complimentary flow coupling filters comprising a blower flow coupling filter and an oxygen flow coupling filter. The oxygen flow coupling filter may comprise a low-pass coupling filter, and the blower flow coupling filter may comprise a high-pass coupling filter relative to the oxygen flow coupling filter. The pair of complimentary flow coupling filters can be configured to be complimentary to partition actuator influence over different bands of frequency.

At step 250 of the method, each of the blower flow coupling filter and the oxygen flow coupling filter generate an output comprising an input flow trajectory for the blower flow controller and an input flow trajectory for the pressurized oxygen source flow controller, respectively. These inputs are provided to the blower flow controller and the pressurized oxygen source flow controller.

At step 260 of the method, the blower flow controller adjusts the speed of the air blower and/or the oxygen flow controller adjusts the pressurized oxygen source proportional flow valve based on the received target pressure and target oxygen mix and further based on the respective received input flow trajectory.

According to an embodiment, the single-limb non-invasive ventilator can further comprise a complimentary filter in feedback with the pressure controller, which is configured to receive a pressure measurement from a ventilator pressure sensor and to receive a proximal pressure measurement from a proximal pressure sensor of the patient circuit. The complimentary filter can be configured to generate a single pressure signal to the pressure controller by blending the received pressure measurement from the ventilator pressure sensor and the received proximal pressure measurement from the proximal pressure sensor. The complimentary filter can be further configured to blend the received pressure measurements using complimentary frequency bands with the proximal pressure sensor signal at a low frequency and the ventilator pressure sensor signal at a higher frequency.

Figure 3:
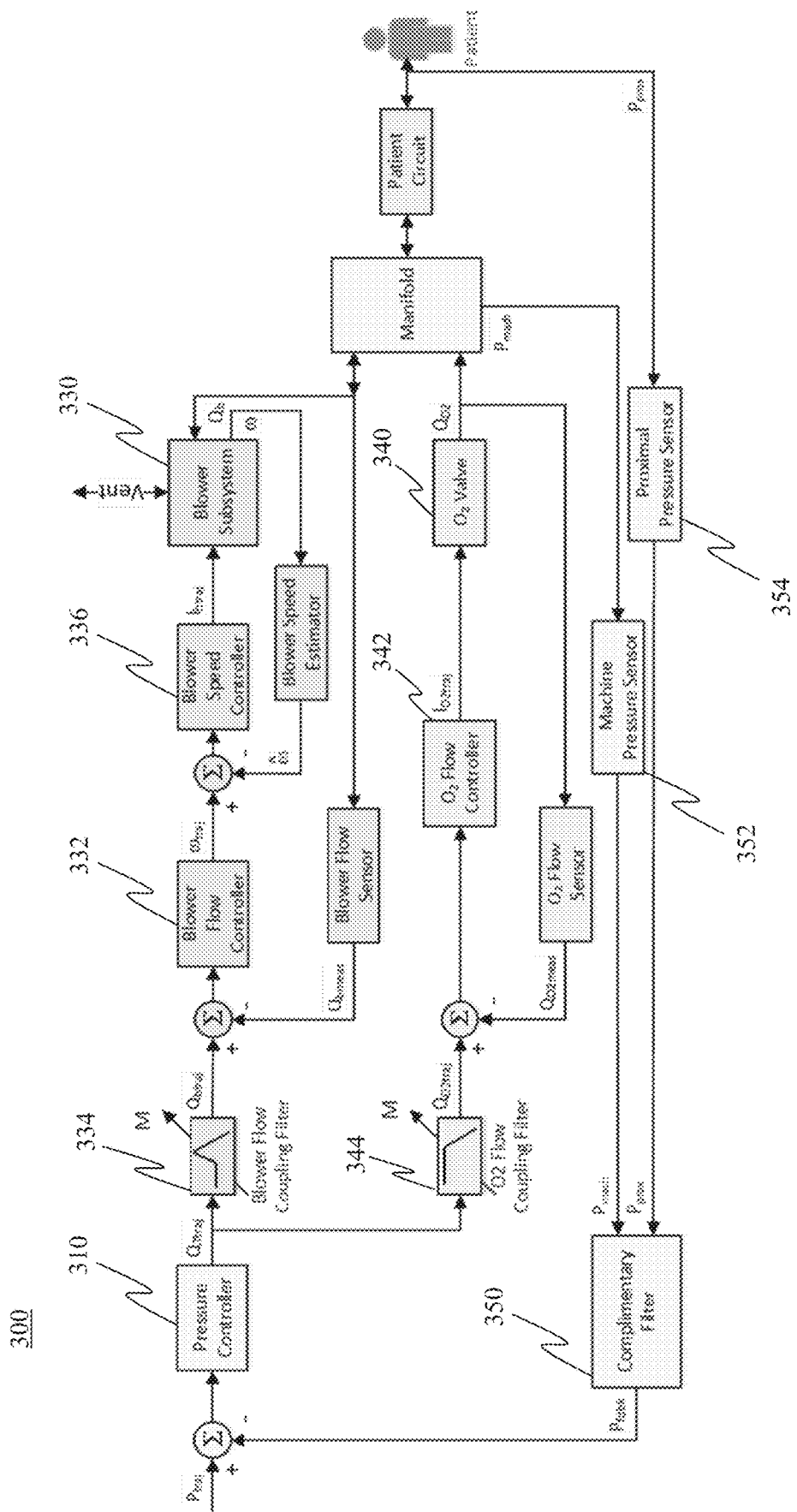
FIG. 3 is a schematic representation of a non-invasive ventilator system, in accordance with an embodiment.

Referring to FIG. 3, is an embodiment of a single-limb non-invasive ventilator system 300 configured to control oxygen mix pursuant to a target pressure and target oxygen mix. The non-invasive ventilator system can be any of the embodiments described or otherwise envisioned herein. The components of the non-invasive ventilator system are described with regard to FIG. 3, and are further described in greater detail below.

According to an embodiment, the system may comprise a single pressure controller 310 configured to generate a total flow trajectory and/or to generate an output used to generate a total flow trajectory, such as by a controller 120 of the system.

The system further comprises a blower 330 comprising a blower flow controller 332 and an air blower speed controller 336 controlling blower flow. Thus, the blower flow controller and the blower speed controller can control flow input into the system. The blower and the blower components can be any components suitable for adequate control of the system.

The system further comprises a pressurized oxygen source downstream of the blower, and includes an oxygen flow controller 342 and a proportional flow valve 340 controlling oxygen flow. Thus, the oxygen controller and oxygen flow valve can control oxygen flow into, and oxygen mix of, the system. The pressurized oxygen source can be any source of oxygen.

The system further comprises a pair of complimentary flow coupling filters, including one blower flow coupling filter 334 and one oxygen flow coupling filter 344. The filters may comprise any filters suitable to perform the functions described or otherwise envisioned herein. For example, the oxygen flow coupling filter can be a low-pass coupling filter, and the blower flow coupling filter can be a higher-pass coupling filter relative to the oxygen flow coupling filter. The pair of complimentary flow coupling filters can be configured to be complimentary to partition actuator influence over different bands of frequency.

The controller 120 of the system is configured to perform one or more functions of the system. Many or all of the controlling functions can be performed by the controller 120. For example, the controller may be configured to: (i) provide the generated total flow trajectory from the blower pressure controller to the pair of complimentary flow coupling filters; and (ii) receive an output from each of the blower flow coupling filter and the oxygen flow coupling filter, comprising an input flow trajectory for the blower flow controller and an input flow trajectory for the pressurized oxygen source flow controller, respectively.

Accordingly, the blower flow controller and/or oxygen flow controller can adjust, based on the input flow trajectory and the target pressure and target oxygen mix, the blower speed or flow controller and/or the pressurized oxygen source proportional flow valve.

According to an embodiment, the system further comprises a complimentary filter 350 in feedback with the pressure controller. The complimentary filter can be configured to receive a pressure measurement from a ventilator pressure sensor 352 and to receive a proximal pressure measurement from a proximal pressure sensor of the patient circuit 354. The complimentary filter can be configured to generate a single pressure signal to the pressure controller by blending the received pressure measurement from the ventilator pressure sensor and the received proximal pressure measurement from the proximal pressure sensor. Further, the complimentary filter can be configured to blend the received pressure measurements using complimentary frequency bands with the proximal pressure sensor signal at a low frequency and the ventilator pressure sensor signal at a higher frequency.

According to an embodiment, the system comprises a dynamic, ratiometric approach to mix control comprised of an oxygen flow coupling filter:

$$Q_{O2traj} = \frac{(M-21)\omega_o^2}{(100-M)s^2 + 2\zeta\sqrt{79(100-M)}\,\omega_o s + 79\omega_o^2} Q_{Ttraj} \quad \text{(Eq. 1)}$$

And further comprises a blower flow coupling filter:

$$Q_{btraj} = \frac{(100-M)(s^2 + 2\zeta\omega_o s + \omega_o^2)}{(100-M)s^2 + 2\zeta\sqrt{79(100-M)}\,\omega_o s + 79\omega_o^2} Q_{Ttraj} \quad \text{(Eq. 2)}$$

Figure 4:
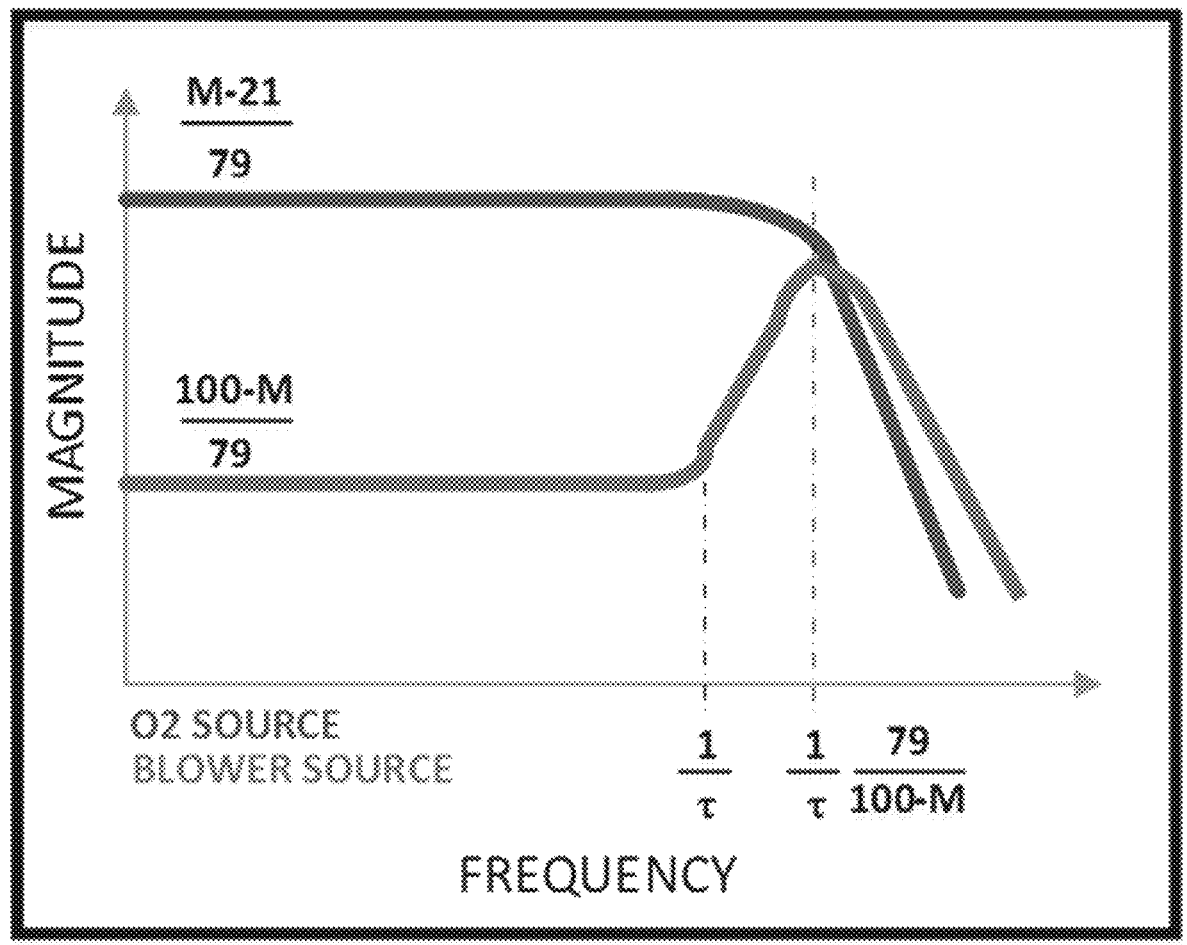
FIG. 4 is a graph showing flow coupling filters frequency response for oxygen and blower (flow) controls, in accordance with an embodiment.
Figure 5:
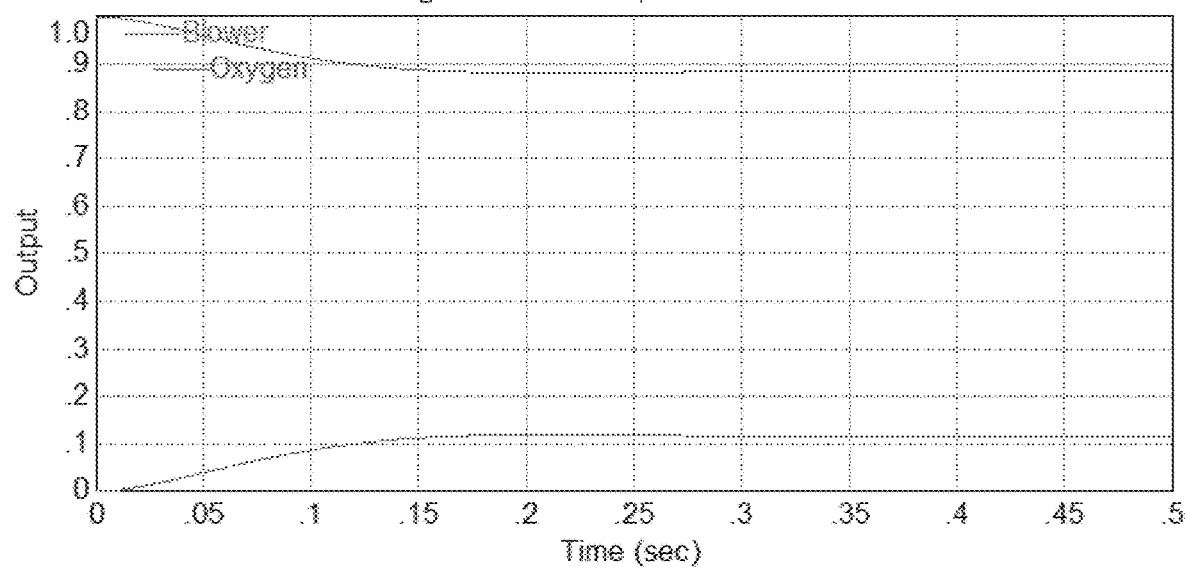
FIG. 5 is a graph demonstrating flow coupling filters with a step response at mix=30%, in accordance with an embodiment.
Figure 6:
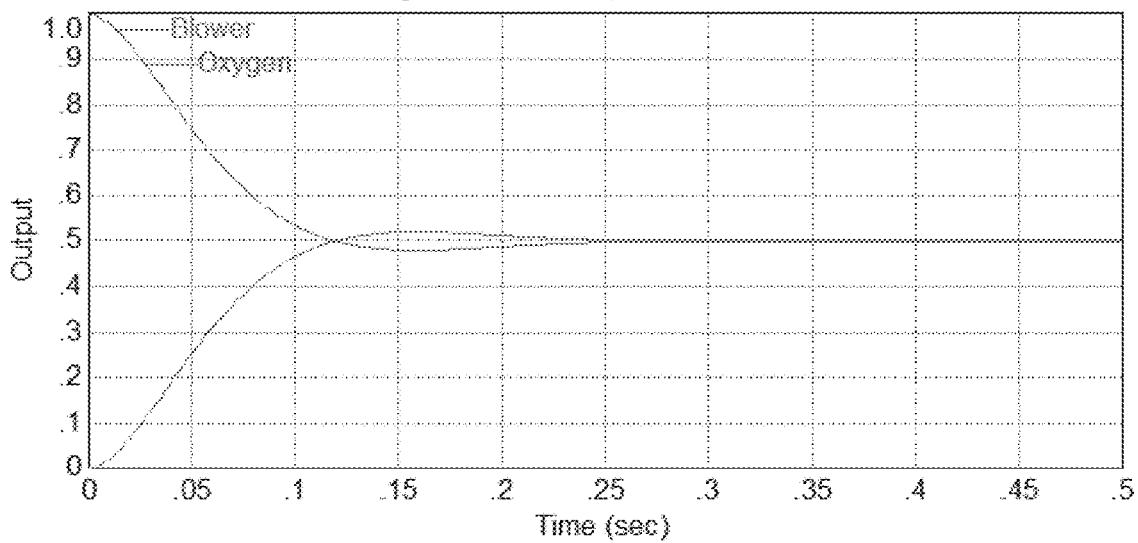
FIG. 6 is a graph demonstrating flow coupling filters with a step response at mix=60.5%, in accordance with an embodiment.
Figure 7:
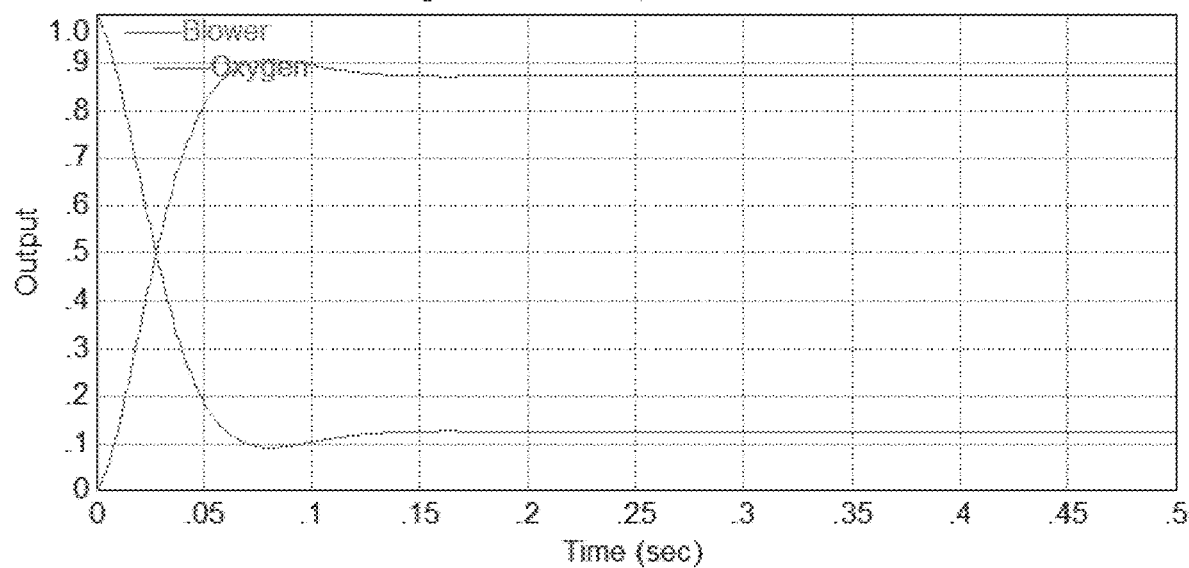
FIG. 7 is a graph demonstrating flow coupling filters with a step response at mix=90%, in accordance with an embodiment.

For equations 1 and 2, the flow coupling filters for oxygen and blower span the full range of mix from 21 to 100%. An example frequency response of the flow coupling filers are shown in FIG. 4. The variable cutoff frequency of the filter depends on the mix target. Steady state mix ratio is achieved in all cases at the extreme settings of 21 and 100%; all dynamics vanish. Example step response of the filters alone is shown in FIGS. 5-7 illustrating the symmetry (complementary action); lead action on the blower side and lag on the oxygen side. It also shows the variable rise time that depends on the mix target. FIG. 5 demonstrates flow coupling filters, with a step response at mix=30%; FIG. 6 demonstrates flow coupling filters, with a step response at mix=60.5%; FIG. 7 demonstrates flow coupling filters, with a step response at mix=90%.

Control Structure; Blower Cascade Structure

The coupling filters derived above receive the same input: the output of the pressure controller; the total flow trajectory. The coupling filter outputs provide respective input flow trajectories for the blower (air) and oxygen valve flow control loops according to the set mix. The coupling filters naturally include the algebraic scaling factors to achieve proper mix at steady state, but equally important, frequency response characteristics that the blower and oxygen valve to respond with unvaried stable control from lowest to highest mix settings. FIG. 3 is a schematic representation of a cascade controller, and illustrates how the coupling filters are used to connect the pressure controller with the two flow control loops for blower and oxygen valve.

Thus, FIG. 3 also shows a multi-level cascade feedback architecture as the blower pressure controller. This architecture maximizes inner-loop stiffness and manages disturbance rejection at each sub-level such that the pressure controls at the top most level are able to achieve high performance. Starting with the inner most part of the cascade, the levels include (a) a current feedback loop that minimizes the influence of back-emf and overcomes the intrinsic electrical time constant of the motor (not shown in the figure), (b) a blower speed feedback loop, that linearizes speed controls, rejects motor load disturbances, and hard-limits to maximum speed constraints with high precision (c) a flow feedback loop that helps reject pressure disturbing influences caused by patient flow demand, cough, and partial circuit occlusions, and at the top level (d) a pressure feedback loop that accurately tracks the applied pressure trajectories.

The system includes a speed controller that bridges the flow and current controllers and rejects viscous frictional and torque related disturbances. The speed controller relies on a model based motor speed observer that supplements tachometer speed readings at low speed, providing the ability to control blower speed at very low rates. This greatly improves the ability to control pressure transients during exhalation with the blower.

The system includes inter-cascade compensator communications that provide feed-forward speed advantages and improved anti-windup capabilities. There is a feed-forward connection between the pressure error and blower current command, and an anti-windup feedback connection from the blower speed limits back to the pressure loop integrator.

The system includes a one fits all applications architecture. Besides suiting the purpose of breath delivery, the cascade controller architecture can serve other applications including system services, standby, and flow therapy modes.

Adaptive Pressure Control Using Lung Resistance Estimate

Figure 8:
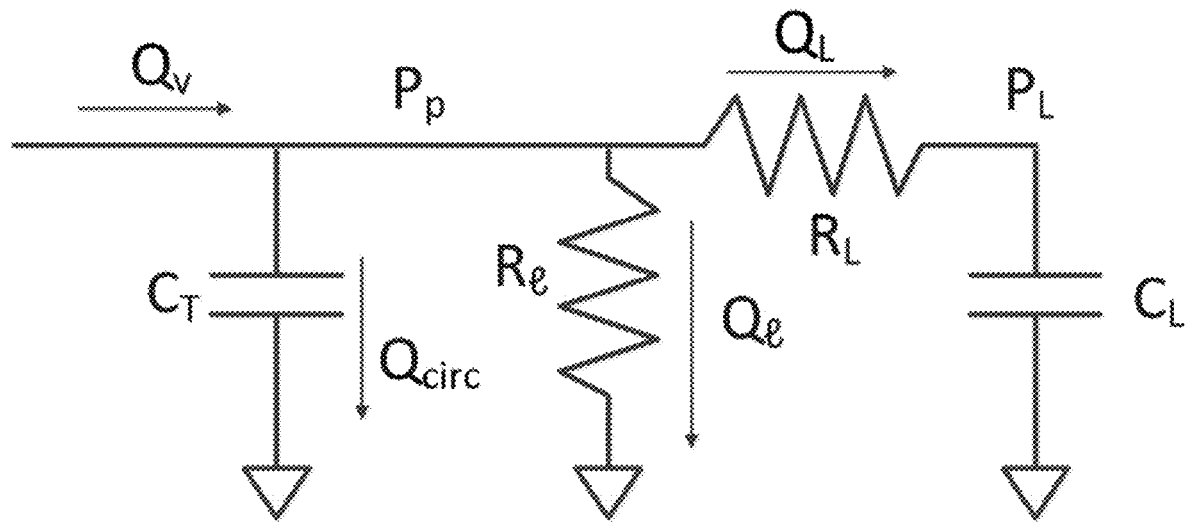
FIG. 8 is a lung-patient model using a circuit analogy for pressure controller design, in accordance with an embodiment.

Pressure control overshoot is associated with the particular load dynamics (lung and circuit time constants) however depending on the controller structure and associated gains. The lung and circuit can be modeled in terms of a linear circuit model (system analogy) as shown in FIG. 8. Thus, FIG. 8 shows a lung-patient model using a circuit analogy for pressure controller design.

Ventilator net flow is Qv, lumped patient tubing compliance is CT, lumped circuit leak resistance is RL with net circuit leak flow, QL. Pp is the proximal pressure, QL is the lung flow, RL the lung resistance, PL the lung pressure and CL the lung compliance.

Given this system and the linear parameter assumptions one can write the following second order, real pole transfer function from ventilator net flow to proximal pressure as:

$$\frac{P_p(s)}{Q_v(s)} = \frac{R_\ell(sC_LR_L + 1)}{s^2(C_TR_\ell C_LR_L) + s(C_TR_\ell + C_LR_L + R_\ell C_L) + 1} \quad \text{(Eq. 3)}$$

Figure 9:
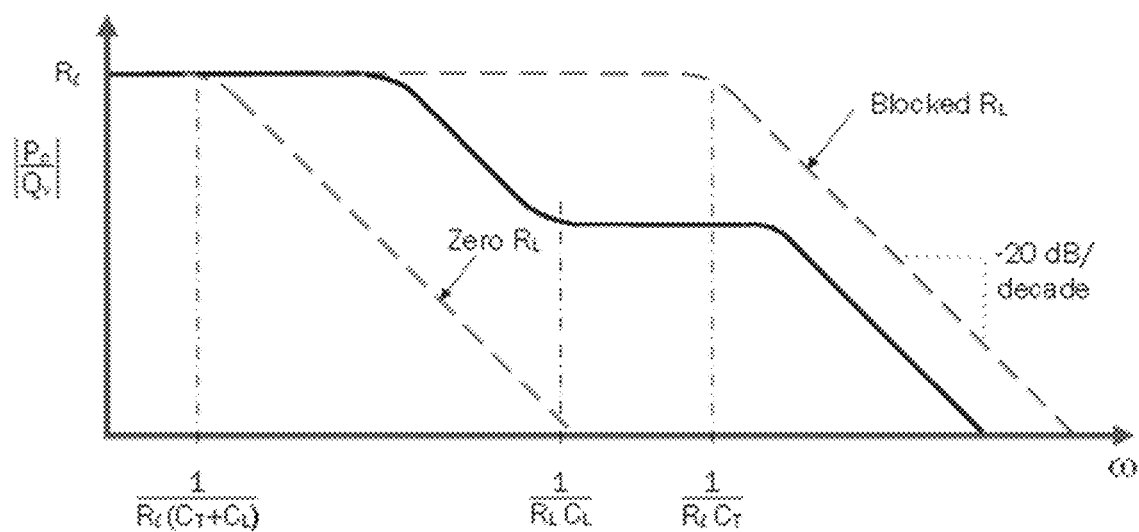
FIG. 9 is a graph showing the frequency response landscape of lung circuit dynamics with leak, in accordance with an embodiment.

The magnitude frequency response of this transfer function is plotted in FIG. 9 (i.e., a graph showing the frequency response 'landscape' of lung circuit dynamics with leak). In general, the frequency response function is illustrated by the bold black line with low frequency (steady state) gain equal to the circuit leak resistance. As leak resistance becomes very high the zeroth order term in Equation 26 vanishes resulting in the RCC model that's been described in earlier papers to represent invasive systems (where leak is negligible):

$$\frac{P_p(s)}{Q_v(s)} = \frac{(sC_LR_L + 1)}{(C_L + C_T)s\left(\frac{C_LR_LC_T}{C_L + C_T}s + 1\right)} \quad \text{(Eq. 4)}$$

But the frequency response Equation 4 can also be bounded in terms of another parameter; the extreme bounds of lung resistance $R_L$. For $R_L \to 0$ the transfer function is reduced to a first order response with cutoff according to the time constant associated with circuit leak resistance and the combined compliance of the circuit and lung:

$$\frac{P_p(s)}{Q_v(s)} = \frac{R_\ell}{sR_\ell(C_L + C_T) + 1} \quad \text{(Eq. 5a)}$$

For $R_L \to \infty$, a blocked state, the transfer function is again reduced to a first order response however with cutoff according to the time constant associated with circuit leak resistance and compliance of the patient circuit alone.

$$\frac{P_p(s)}{Q_v(s)} = \frac{R_l}{sR_\ell C_T + 1} \quad \text{(Eq. 5b)}$$

In either of these extreme cases, (Equation 5a) or (Equation 5b), the zero of the transfer function vanishes. But for the general case, the second order system, the zero determined by the lung time constant links two cutoff frequencies existing between the two poles, and these are bounded by the extremes described above. In this general case the two frequencies are hopelessly entangled in terms of reducing their values analytically, at least for any practical purposes.

Realizing the system in these terms provides a framework for direct synthesis of a pressure control solution; one in which one attempts to force the open loop system to appear as a simple integrator. One just needs to determine a loop shaping filter that effectively 'cancels' the dynamics of the system but assuring the remaining presence of an integrator. One can simply define the loop shaping filter to be the inverse of (3) with an integrator:

$$C(s) = K\left(\frac{s^2(C_TC_LR_L) + s\left(C_T + C_L\left(1 + \frac{R_L}{R_\ell}\right)\right) + \frac{1}{R_\ell}}{S}\right)\left(\frac{1}{sC_LR_L + 1}\right), \quad \text{(Eq. 6)}$$

and set the value of K to achieve the desired closed loop cutoff frequency. Of course anti-windup measures must be properly included to manage windup in the event of saturating the flow controls. But as a linear compensator (Equation 6) is easily recognized as a PID (proportional integral derivative) filter cascaded with a lag filter. Absorbing the loop gain, K, the PID gains become:

$$K_D = KC_TC_LR_L \quad \text{(Eq. 7)}$$

$$K_p = K\left(C_T + C_L\left(1 + \frac{R_L}{R_\ell}\right)\right) \quad \text{(Eq. 8)}$$

$$K_i = \frac{K}{R_\ell} \quad \text{(Eq. 9)}$$

In theory; to be precise, linear systems theory, this would all work. The issue is that all of these parameters can change depending on a number of factors.

The tubing compliance, $C_T$ can be calibrated prior to patient attachment, and although condensed water in the circuit might cause a slight increase in compliance, a larger effect would come by the circuit operating at a higher temperature than what it was calibrated at. An increase in operating (absolute) temperature of the gas causes a proportional increase in compliance for a fixed compliance boundary (rigid boundary). This can be corrected if an assumed operating temperature, or gas temperature measurement is provided. If the boundary is flexible, the tubing compliance may also be different at different operating pressures as increasing pressure causes the geometric volume to increase.

The largest change/difference in the lung compliance, $C_L$ is the particular patient although the lung compliance for a particular patient can vary as disease progresses or improves, or as the patient changes positions in bed (laying on back, side etc.). An even larger effect can be due to strong active breathing by the patient which tends to appear as 'added compliance'. According to the linear model lung compliance cannot be easily differentiated from patient effort. Even though a clinician can measure compliance before or during applied ventilation, these measurements should not be assumed as fixed. Some means of on-line, real time estimation of lung compliance should be arranged so the control can remain robust. Unlike tubing compliance, lung compliance will not be affected by temperature as airways and the huge surface area of the lung regulate the temperature near 37 deg C.

The lung airway resistance $R_L$ has similar issues as the lung compliance and should be estimated on line, but the main issue is that flow resistance, at least the upper airways or ETT cannot always well fit a linear model. The flow, pressure relation is better approximated as quadratic; as a 2 parameter model. The resistance given as a function of the flow. So for lung resistance:

$$R_L(Q_L) = K_2|Q_L| + K_1 \quad \text{(Eq. 10)}$$

Thus resistance changes continuously as flow changes.

The leak resistance $R_e$ also follows the same model, of course with different coefficients:

$$R_\ell(Q_\ell) = K_2|Q_\ell| + K_1 \quad \text{(Eq. 11)}$$

Although fixed (known) leak resistance can be calibrated before patient attachment, or else determined a-priori from factory measurements (specifically mask leak or exhalation port leak), provision should be included for estimating unknown leak as leak can increase (or decrease for that matter) during breath delivery.

Choices considered for the pressure control include:
1. Fix all the parameters to some nominal values to compromise between overshoot at low airway resistance and oscillation at high resistance. It is known that this does not work very well as patient load approaches extreme dynamics (slow and fast lung time constants).
2. Build an estimator to continually update the parameters and thus the PID gains in real time. This is an improvement on (1.) but it assumes the 'frozen parameter' assumption for linear parameter varying systems; that the system is not only stable at specific (frozen) states of operation, but also between states as the system transitions between them. This assumption is not always true, there is no simple way to assure it, and so there is considerable risk in choosing continuous updates besides the complexity of designing the estimators.
3. Use a gain assignment approach, focusing on a smaller set of or single parameter; those that have a more significant effect on the stability and response. Update appropriate gains on a breath by breath basis.

For this disclosure the last option was selected to avoid complexity of a more extensive multi-state estimator, however nothing technically prohibits using method (2.). It was experimentally determined that the Ki and Kd gains could be fixed and that Kp could be simply adjusted according to a single system parameter estimate of $\hat{K}_L$ using an assumed single parameter quadratic model. $\hat{K}_L$ is equal to K2 in Equation 33 assuming that K1<<K2:

$$K_{pP}=\min(\max(-0.1714\hat{K}_L+18.857),12),20)$$ (Eq. 12)

where $\hat{K}_L$ is the airway resistance estimate with units in cm $H_2O/(lps)^2$.

Figure 10:
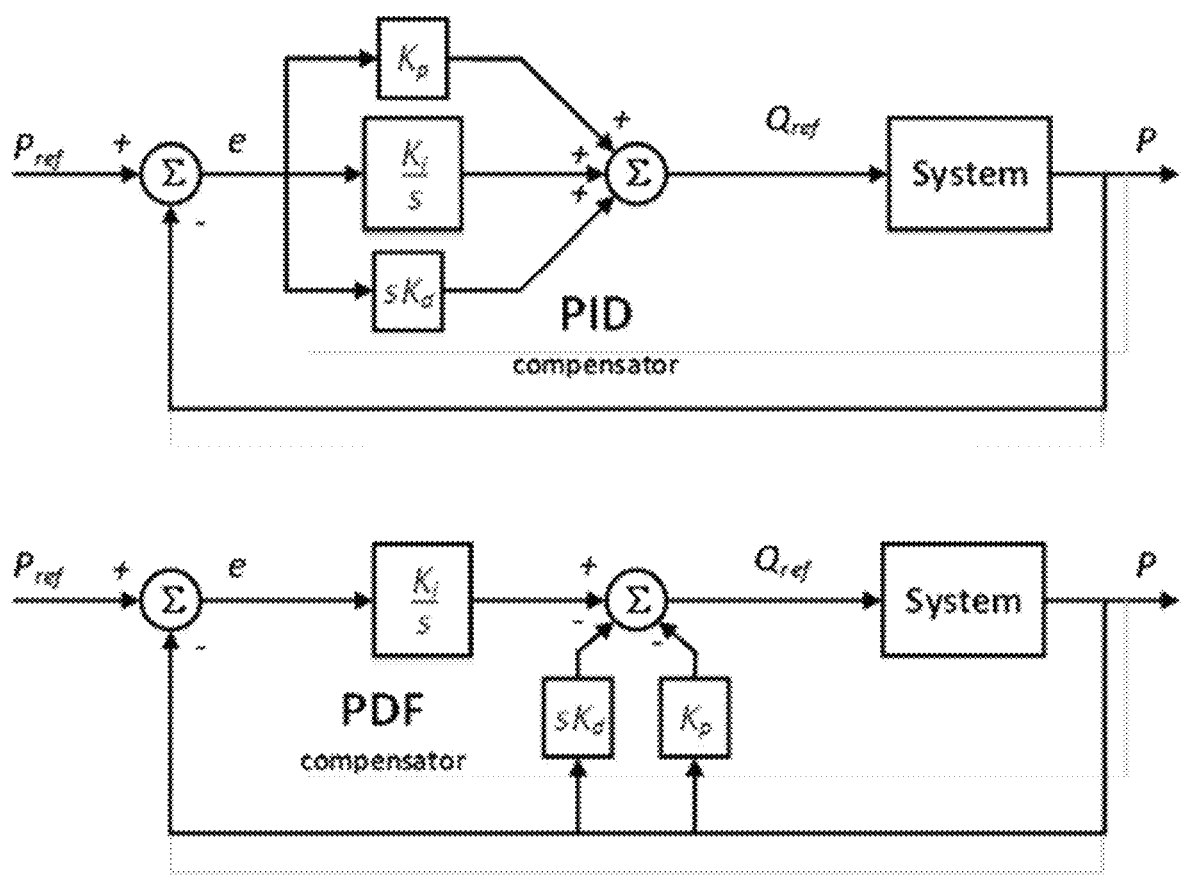
FIG. 10 is a graph showing pseudo derivative feedback compared to proportional integral derivative control, in accordance with an embodiment.

To further avoid pressure overshoot, the PDF (pseudoderivative feedback) version of control is used. This approach feeds back the compensator non-integral components after the integrator rather than before. In other words proportional and derivative feedback the measurement, P rather than the measurement error, e. The PDF structure is compared with the PID structure in FIG. 10. Thus, FIG. 10 shows pseudoderivative feedback (PDF) compared to PID control; PDF preserves the same characteristic function as PID control however removes the zero introduced by the PID compensator.

Complimentary Filter for Pressure Control

Figure 11:
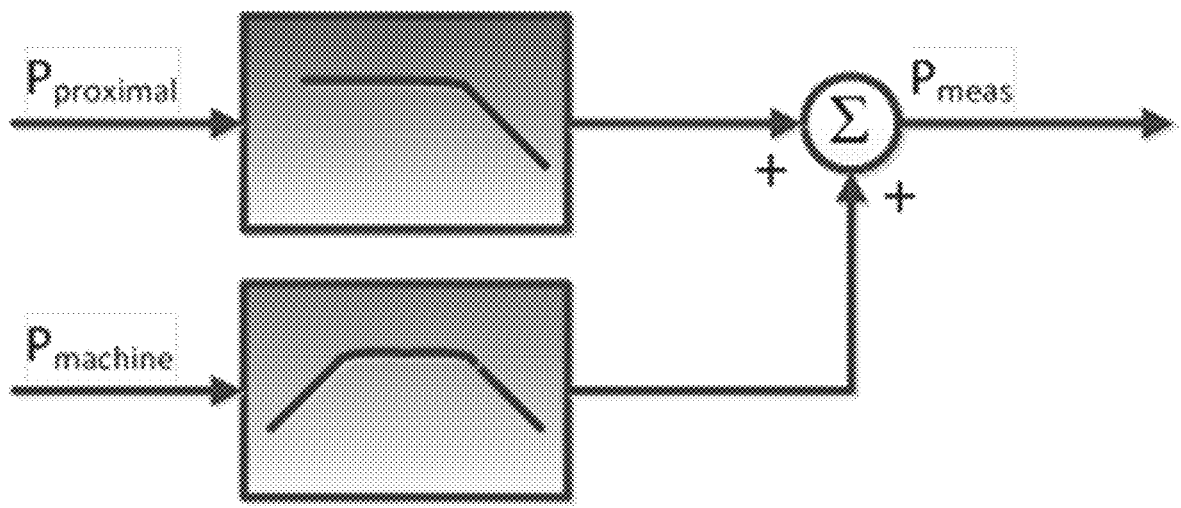
FIG. 11 is a block diagram of the complimentary filter used in pressure feedback control, in accordance with an embodiment.

For the pressure controller, another different complimentary filter is used for feedback of pressure. This filter combination blends the machine and proximal pressure signals into a single signal for pressure feedback control. Blending is done across complimentary frequency bands: the proximal sensor at low frequency and the machine sensor at higher frequencies. The machine signal, with less delay provides a stable, but faster blower response, and the prox signal, accurate proximal pressure at steady state. A block diagram of the complimentary filter used in pressure feedback control is illustrated in FIG. 11. For the new method, the crossover frequency between the low pass filter and the bandpass filter was increased giving proximal pressure more weight than in the previous design.

Proximal Pressure Estimation During Purge

High performance pressure controls are possible as long as there is integrity in the feedback measurements. But for a pneumatic design structure that must periodically purge the proximal sense line (to prevent intrusion of water and mucous), the pressure is momentarily not present. This 'opens' the closed loop, and this can cause instability. For high performance control the last good measurement cannot be simply 'latched' or suspended for the duration of the purge. This still constitutes a sensor outage; an open loop situation. The best way of maintaining stable operation during this interval, that lasts only a few hundred milliseconds, is to estimate the proximal pressure using other available pressure and flow sensors. The estimate needs to be as close as possible to the normal measurement in terms of magnitude, phase and delay to serve as a proxy. Feedback controls and stability are sensitive to all of these factors. So delay (propagation delay) must also be part of the estimate.

Figure 12:
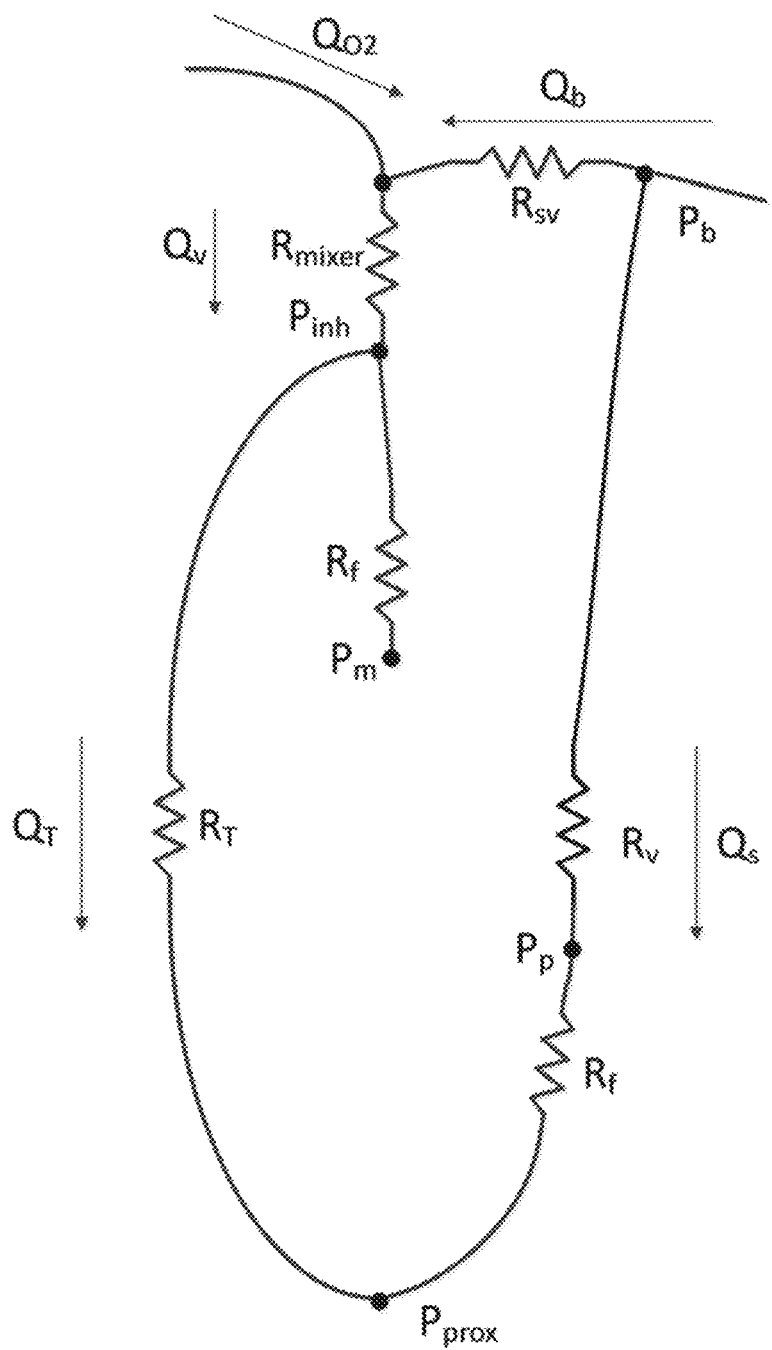
FIG. 12 is a schematic representation illustrating plumbing that accomplishes the shunt of blower pressure to proximal line when the purge valve, Rv is opened, in accordance with an embodiment.

According to an embodiment, pressure from the blower manifold pressure sensor (blower pressure sensor) is shunted into the proximal pressure sensor connection to expel any condensed water that may have accumulated, migrated into the end of the proximal pressure sense line. FIG. 12 illustrates schematically how the purge flow is shunted from the blower pressure through the purge valve represented by resistance, Rv. Thus, FIG. 12 is a schematic representation illustrating plumbing that accomplishes the shunt of blower pressure to prox line when the purge valve, Rv is opened. Thus the integrity of Pm is maintained during purge. For single-limb NIV, this may be done every minute at the start of the breath. And during this interval the proximal sensor will sense a superposition, a pressure value that exists somewhere between the actual blower and proximal pressures—largely determined by pressure drops that occur from sensor filters and the purge valve restriction. These parameters are difficult to estimate, most likely different in every system.

According to an embodiment, therefore, the methods and systems described or otherwise envisioned herein may use the one remaining pressure during purge, the machine pressure, Pm and the flow sensor measurements from the ventilator, QO2 and Qb. This requires a-priori parameters of circuit compliance CT and circuit propagation delay, that can be determined as part of the patient circuit calibration.

Figure 13:
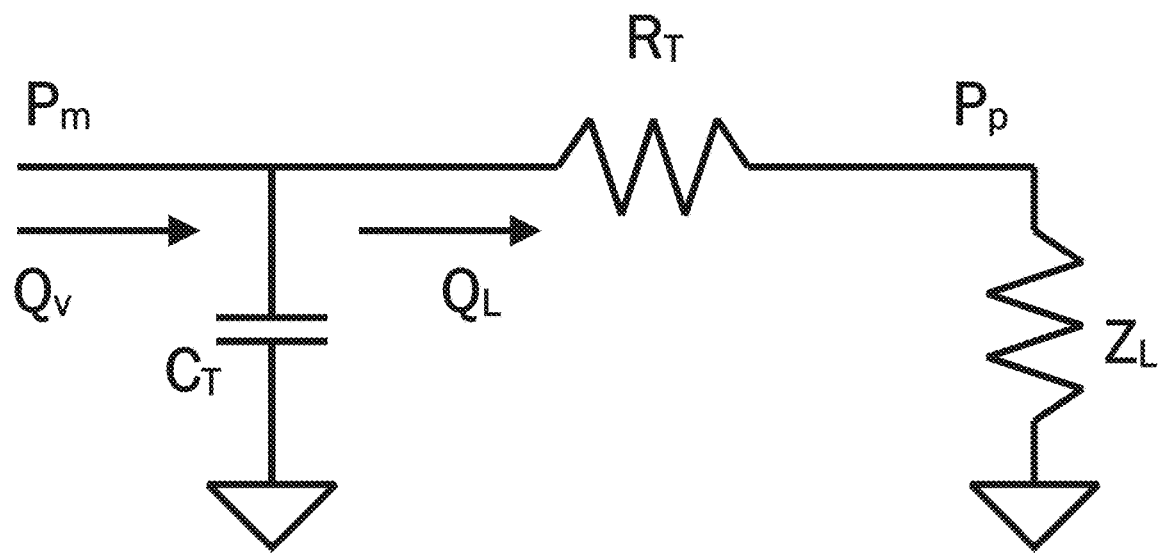
FIG. 13 is a circuit model assumed for a proximal pressure estimator that includes patient circuit time constant, in accordance with an embodiment.

Referring to FIG. 13 is a circuit model assumed for a proximal pressure estimator that includes patient circuit time constant. The position of the lumped circuit compliance relative to the tubing resistance preserves machine pressure and ventilator flow as inputs. Thus, FIG. 13 illustrates the assumed circuit model and generalized patient load impedance, $Z_L$, which does not need to be known but rather serves to illustrate that a non-zero proximal pressure occurs, $P_p$. $R_T$ is the tubing resistance, $Q_v$ is the net flow (QO2 plus Qb) from the ventilator, $C_T$ the patient tubing compliance, and $P_m$ the machine pressure measured at the inlet to the patient tubing.

Unlike prior models used for estimating circuit parameters, the (lumped) tubing compliance is chosen to exist on the upstream (left) side of the (lumped) tubing resistance. This key choice assures that the compliance, an essential dynamic parameter, is preserved in the model formulation. The circuit analogy written as a linear model is extended to a nonlinear model by allowing the tubing resistance to be a function of the flow that crosses it:

$$R_T(Q_L)=K_{T2}|Q_L|+K_{T1}$$ (Eq. 13)

The machine pressure occurs by the net flow into the tubing compliance:

$$P_m = \frac{1}{sC_T}(Q_V - Q_L) \quad \text{(Eq. 14)}$$

And the pressure drop from machine to proximal pressure is:

$$P_m - P_p = Q_L R_T \quad \text{(Eq. 15)}$$

Lastly the nonlinear resistance of the tubing is substituted, solve for proximal pressure as an estimate, but furthermore delay this estimate by the delay, D to simulate the same delay incurred as if the sense line were present.

$$\hat{P}_p = (P_m(1 - sC_T R_T) - R_T Q_V) e^{-sD} \quad \text{(Eq. 16)}$$

This formulation provides a very close estimate of the proximal pressure, good enough to serve as a feedback signal in the pressure control during the purge interval. Testing has shown imperceptible difference in pressure control for purge/regular breaths.

The method of obtaining the delay parameter, D is done by running the single limb circuit compliance calibrations. The patient tubing compliance and resistance parameters are all determined, but additionally the machine pressure, actual proximal pressure and net ventilator flow signal measurements are saved to further determine patient circuit delay. After calibration determines the parameters, the un-delayed model proximal pressure output is compared with the (delayed) measured pressure. Then successive estimates for D are derived and applied to the un-delayed estimate such that the group sample difference is minimized. The value of D is rounded to the nearest step size used in the control, ΔT.

Figure 14:
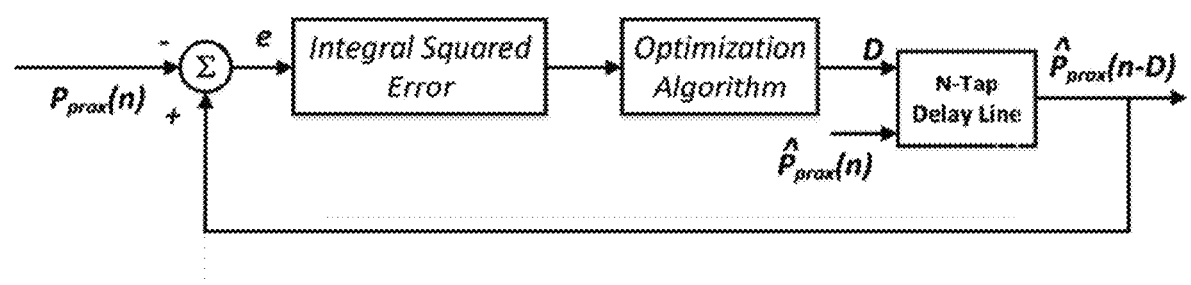
FIG. 14 is a block diagram method for determining delay in proximal pressure measurement, in accordance with an embodiment.

To illustrate one embodiment of the method, an N-tap delay line is used in batch, closed loop process. Step by step, the samples of measurement and delayed estimate are differenced, and the squared error integrated over the batch. The result is then input to an optimization routine (e.g. Powell's gradient search) which results in a delay index that is quantized according to the sampling interval of the system timing. For various embodiments, that is 0.001 sec, although other values are possible. The delay index selects the number of delay taps to apply to the estimated proximal pressure samples for the next iteration. When error reaches the threshold set by the optimizer, the process ceases with the estimated delay. Referring to FIG. 14, in one embodiment, is a block diagram method for determining delay in proximal pressure measurement.

Figure 15:
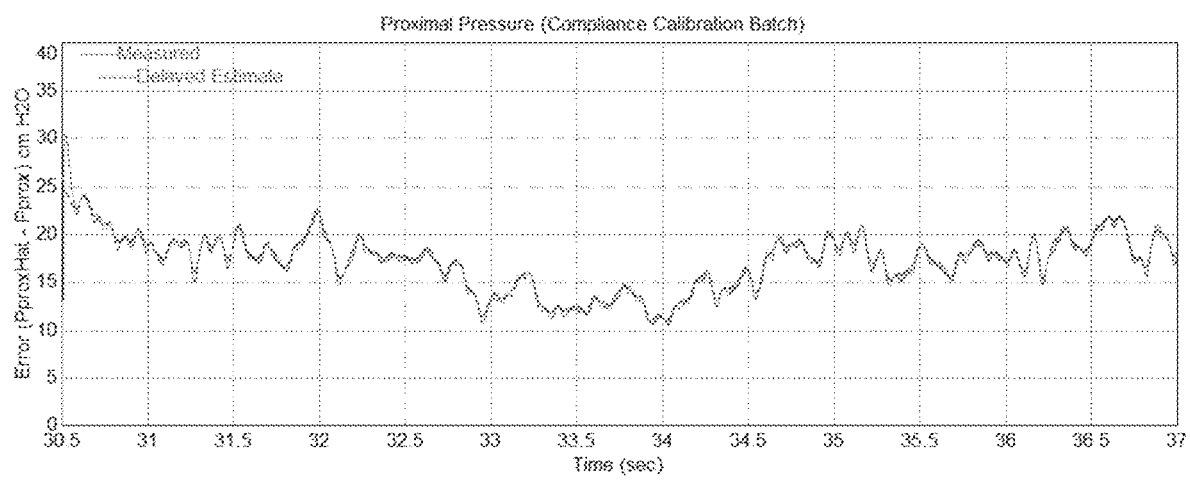
FIG. 15 is an example batch pressure sample to obtain delay parameter where the actual delay is 7 msec, in accordance with an embodiment.
Figure 16:
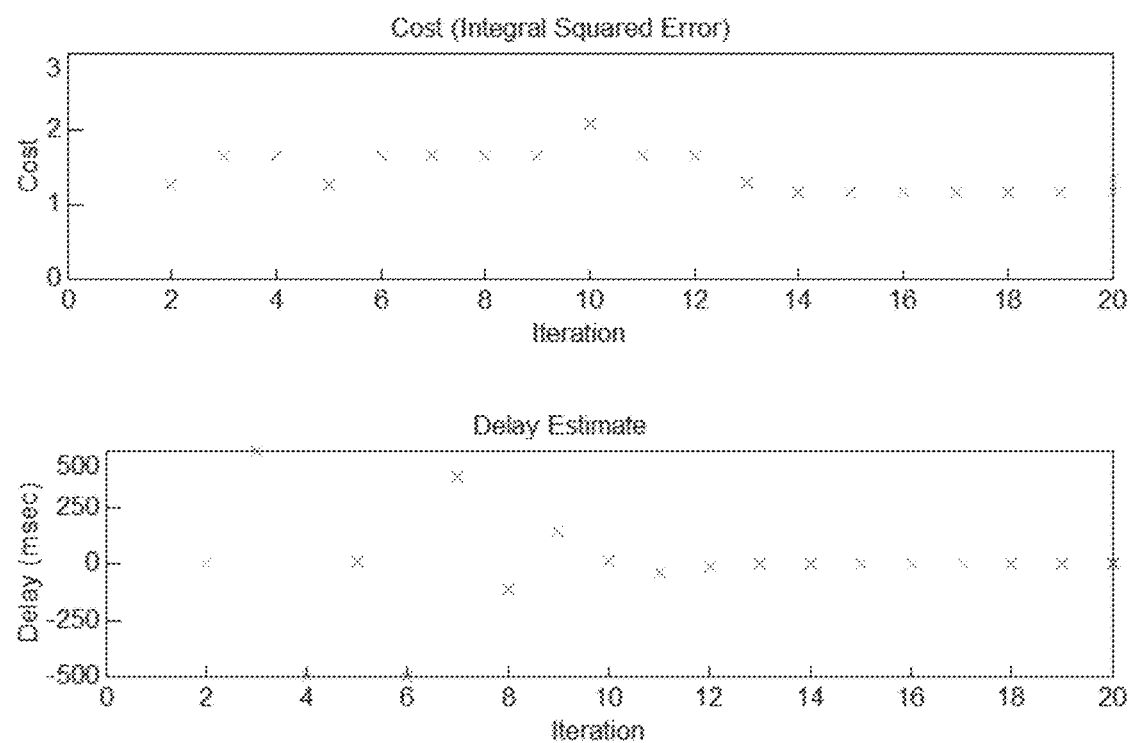
FIG. 16 is a plot of cost function and delay estimate, with the upper plot showing the cost (integral squared error), and the lower plot showing an estimate of delay, in accordance with an embodiment.

The closed loop iteration of the vectors causes a convergence to the actual delay of the circuit as shown by the graph of proximal pressure in FIG. 15, which is an example batch pressure sample to obtain delay parameter where the actual delay is 7 msec. Referring to FIG. 16 is the cost function and delay estimate, with the upper plot showing the cost (integral squared error), and the lower plot showing an estimate of delay which converges to actual value (7 msec) in less than 14 iterations.

Mix Controller

Mix control is primarily facilitated by the flow coupling filters; the filters that couple the total flow output trajectory to the blower and oxygen flow controllers. Each coupling filter receives a corrected mix target; a mix target that is adjusted each breath cycle by a mix controller and based on differences, if any, between the set mix target, and a mix estimate as described further below. The mix controller is sample based meaning that mix convergence is not uniform with time, but rather with number of breaths; information provided at the end of each breath constitutes a sample for the controller. It further improves mix accuracy over what the flow coupling filters alone could not achieve.

Mix Estimator

Rebreathing, a term more often used to describe subsequent inhalation of gas, exhaled from a prior breath, is used more generally in ventilation control design referring to gas that might be subsequently returned to any compartment in the gas path from which it originated. So rebreathing can exist for example in a blower based design when the manifold pressure exceeds the pressure generated by the blower as well as the end expiratory gas being inhaled by the patient. Although the blower might be spinning in a direction that would normally produce forward flow, pressure applied from downstream potential can lead to reverse flow through the blower. This can cause downstream gas to re-enter the blower and blower inlet plenum if such a space exists.

The blower pathway is capable of rebreathing gas from two sources: the patient, and the oxygen flow stream. In the case of the patient, the gas returned to the blower compartment will be the mix from the subsequent breath. Depending on other conditions it is possible that oxygen can be forced into the blower compartment directly from the oxygen valve with reverse blower flow. In this case the volume of gas introduced is at 100% $O_2$ enrichment during this rebreathing interval. In either case existence of rebreathing, and an estimate of gas volume and mix can be tracked using the blower and oxygen flow sensors, then used to correct for subsequent mixing. Thus the oxygen concentration of gas in the blower pathway is not necessarily always 21% oxygen, but can rather be assigned an 'enrichment factor' to account for the rebreathed gas—until blower flow reverses and clears the compartment where the enrichment factor returns to 0.21.

To track rebreathing and the changing enrichment factor, flow states are defined according to the flow directions measured in the oxygen and blower flow sensors. The flow states serve as trigger conditions for transition logic in a state machine that computes and keeps track of oxygen mix in the patient and blower compartments.

It is naturally expected that as flow proceeds that mix spreads out across the gas path channels, but this is not easily modeled quantitatively for real time application and so mix estimates are based on the assumption of plug flow as though distinct boundaries exist between bolus' of different gas mixtures.

Figure 17:
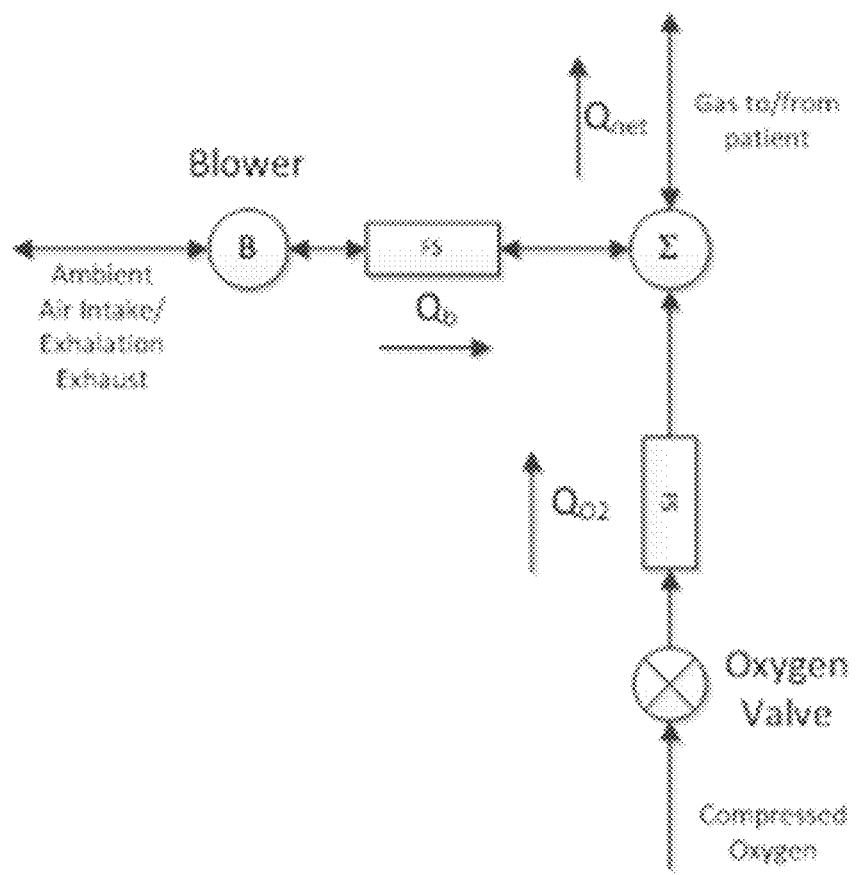
FIG. 17 is a chart of flow state definitions based on a simplified diagram of the gas pathway, in accordance with an embodiment.
Figure 18:
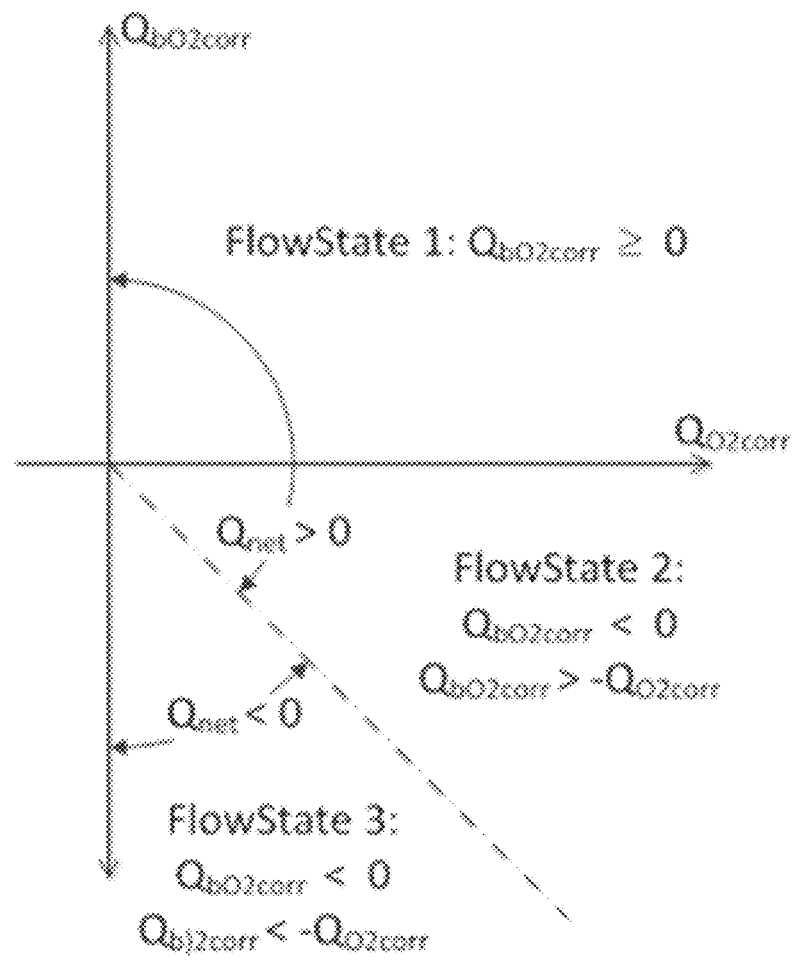
FIG. 18 is a chart of flow state definitions more quantitatively based on the relative size and directions of the blower and oxygen flow, in accordance with an embodiment.

Referring to FIGS. 17 and 18, in one embodiment, is a definition of flow states derived from a conceptual diagram of the blower and oxygen valve flow connections. FIG. 17 is a chart of flow state definitions based on a simplified diagram of the gas pathway of the system. FIG. 18 is a chart of flow state definitions more quantitatively based on the relative size and directions of the blower and oxygen flow. Further details of the flow states described below.

FlowState1: BlowerWithO2fromO2Valve

Flow proceeds in state 1 with oxygen and air from the blower and O2 valve towards the patient. The blower pathway may contain nitrox >0.21 since the rebreathing window for oxygen valve ingress is active.

FlowState1: BlowerClear

Flow proceeds in state 1 with oxygen and air from the blower and O2 valve, both towards the patient. The blower pathway should be cleared of nitrox >0.21 since no rebreathing windows is active.

FlowState1: BlowerWithReturnPatientGas

Flow proceeds in state 1 with oxygen and air from the blower and O2 valve towards the patient. The blower pathway may contain nitrox >0.21 since the rebreathing window patient exhaled flow is active.

FlowState2

In this flow state O2 flow overpowers blower flow so O2 flows into the blower pathway as well as towards the patient.

FlowState3

Flow proceeds in state 3 with oxygen set to zero and patient gas flowing from the circuit back into the ventilator. Integrate only blower flow as enriched gas from the patient.

Figure 19:
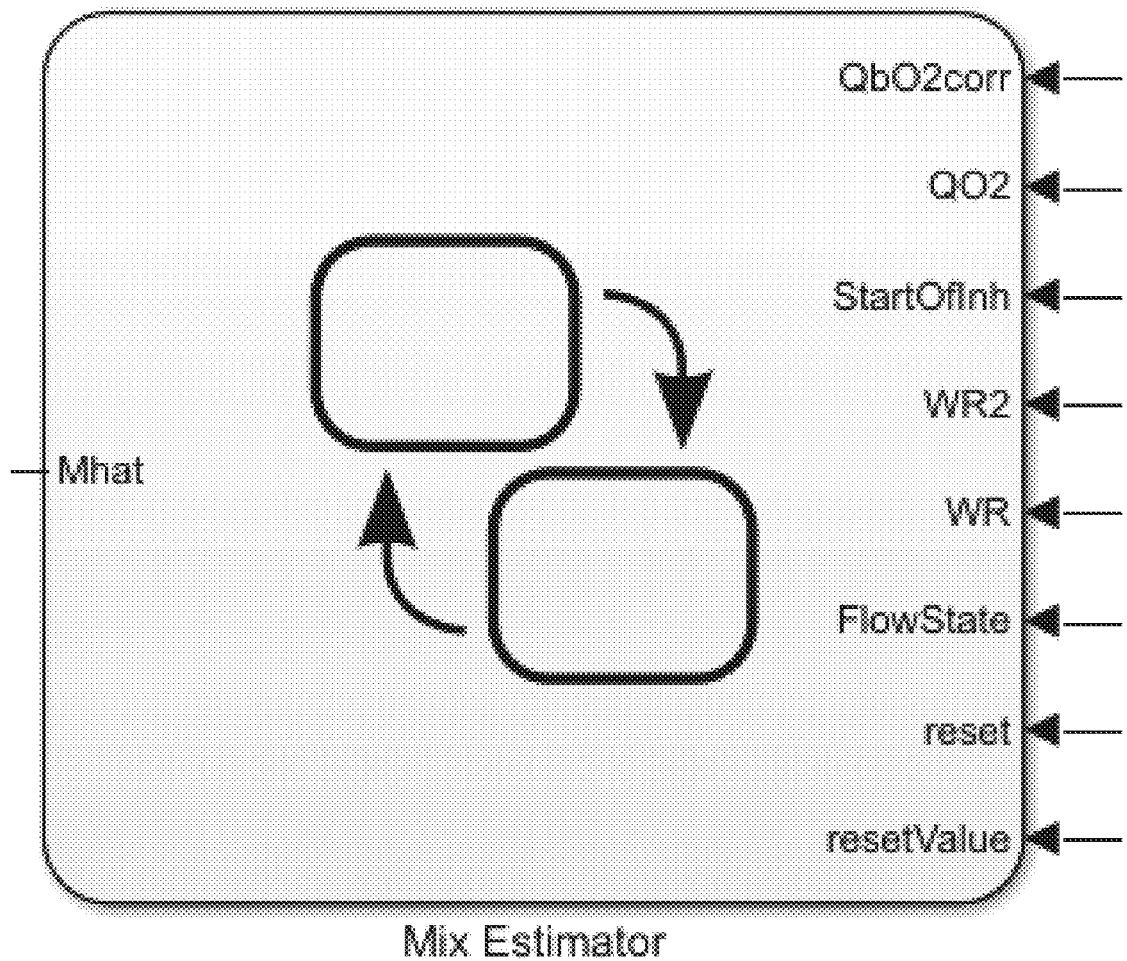
FIG. 19 is a schematic representation of an example state machine mix estimator showing inputs (right side) and output (left), in accordance with an embodiment.

In the state chart, processing transitions between states as breathing progresses. Two estimates are maintained: an estimate of the blower enrichment factor and the estimate of the gas delivered out of the patient port. Referring to FIG. 19, in one embodiment, is an example state machine mix estimator showing inputs (right side) and output (left).

Flow state 3 essentially defines patient exhalation where exhalation of gas flow from the lung at some point exceeds the leak rate present in the patient circuit. Since there are no sensors present to estimate gas enrichment (coming from the patient) one can assume the returning gas is what was issued from the immediate time interval leading up to exhalation. A prior invention simply assumed an average mix, enrichment factor for the return gas, but the present invention considers there may be a significant gradient through the patient circuit. So a last out—first in approach is used. This claim in the invention replays the same mix estimate profile that was issued during inhalation however in reverse, and not according to time, but as a function of volume. This is accomplished by buffering volume and mix estimate data starting immediately after flow state 3. This way the (unknown) occurrence of start of flow state 3 can be started at any point of the breath.

Although the analysis above is examined with regard to certain embodiments, these are provided only as examples. Many other embodiments are described above and envisioned as variations on the single-limb non-invasive ventilation systems and methods.

All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for controlling oxygen mix for a single-limb non-invasive ventilator comprising a pressure controller, and further comprising both an air blower and a pressurized oxygen source, wherein the pressurized oxygen source is downstream of the air blower, wherein the air blower comprises a blower flow controller and the pressurized oxygen source comprises a pressurized oxygen source flow controller, and wherein the pressurized oxygen source comprises a proportional flow valve controlling flow, the method comprising:
- receiving, by the ventilator, a target pressure and target oxygen mix;
- generating, from an output of the pressure controller, a total flow trajectory;
- providing the generated total flow trajectory from the pressure controller to a pair of complimentary flow coupling filters, the pair of complimentary flow coupling filters comprising a blower flow coupling filter and an oxygen flow coupling filter;
- generating an output from each of the blower flow coupling filter and the oxygen flow coupling filter, comprising an input flow trajectory for the blower flow controller and an input flow trajectory for the pressurized oxygen source flow controller, respectively; and
- adjusting, by the blower flow controller and/or oxygen flow controller based on the input flow trajectory and the received target pressure and target oxygen mix, the blower speed and/or the proportional flow valve.

2. The method of claim 1, wherein the oxygen flow coupling filter comprises a low-pass coupling filter.

3. The method of claim 2, wherein the blower flow coupling filter comprises a high-pass coupling filter relative to the oxygen flow coupling filter.

4. The method of claim 1, wherein the pair of complimentary flow coupling filters are configured to be complimentary to partition actuator influence over different bands of frequency.

5. The method of claim 1, wherein the pressure controller comprises a multi-level cascade feedback architecture.

6. The method of claim 1, wherein the single-limb non-invasive ventilator further comprises a complimentary filter in feedback with the pressure controller, the complimentary filter configured to receive a pressure measurement from a ventilator pressure sensor and to receive a proximal pressure measurement from a proximal pressure sensor of a patient circuit.

7. The method of claim 6, wherein the complimentary filter is configured to generate a single pressure signal to the pressure controller by blending the received pressure measurement from the ventilator pressure sensor and the received proximal pressure measurement from the proximal pressure sensor.

8. The method of claim 7, wherein the complimentary filter is configured to blend the received pressure measurements using complimentary frequency bands with a proximal pressure sensor signal at a low frequency and a ventilator pressure sensor signal at a higher frequency.

9. A single-limb non-invasive ventilator system configured to control oxygen mix pursuant to a target pressure and target oxygen mix, comprising:
- a pressure controller configured to generate a total flow trajectory;
- an air blower comprising a blower flow controller and a blower speed controller controlling blower flow;
- a pressurized oxygen source downstream of the air blower and comprising an oxygen flow controller and a proportional flow valve controlling oxygen flow;
- a pair of complimentary flow coupling filters, the pair of complimentary flow coupling filters comprising a blower flow coupling filter and an oxygen flow coupling filter; and
- a controller configured to: (i) provide the generated total flow trajectory from the pressure controller to the pair of complimentary flow coupling filters; and (ii) receive an output from each of the blower flow coupling filter and the oxygen flow coupling filter, comprising an input flow trajectory for the blower flow controller and an input flow trajectory for the oxygen flow controller, respectively, wherein the blower flow controller and/or oxygen flow controller adjust, based on the input flow trajectory and the target pressure and target oxygen mix, a blower speed and/or the proportional flow valve.

10. The single-limb non-invasive ventilator system of claim 9, wherein the oxygen flow coupling filter comprises a low-pass coupling filter.

11. The single-limb non-invasive ventilator system of claim 10, wherein the blower flow coupling filter comprises a high-pass coupling filter relative to the oxygen flow coupling filter.

12. The single-limb non-invasive ventilator system of claim 9, wherein the pair of complimentary flow coupling filters are configured to be complimentary to partition actuator influence over different bands of frequency.

13. The single-limb non-invasive ventilator system of claim 9, further comprising a complimentary filter in feedback with the pressure controller, the complimentary filter configured to receive a pressure measurement from a ventilator pressure sensor and to receive a proximal pressure measurement from a proximal pressure sensor of a patient circuit.

14. The single-limb non-invasive ventilator system of claim 13, wherein the complimentary filter is configured to generate a single pressure signal to the pressure controller by blending the received pressure measurement from the ventilator pressure sensor and the received proximal pressure measurement from the proximal pressure sensor.

15. The single-limb non-invasive ventilator system of claim 14, wherein the complimentary filter is configured to blend the received pressure measurements using complimentary frequency bands with a proximal pressure sensor signal at a low frequency and a ventilator pressure sensor signal at a higher frequency.

* * * * *